(12) United States Patent
Nelson et al.

(10) Patent No.: US 8,440,959 B2
(45) Date of Patent: May 14, 2013

(54) METHOD AND APPARATUS FOR AUTOMATED SPECTRAL CALIBRATION

(75) Inventors: Matthew Nelson, Harrison City, PA (US); Patrick Treado, Pittsburgh, PA (US)

(73) Assignee: ChemImage Corporation, Pittsburgh, PA (US)

( * ) Notice: Subject to any disclaimer, the term of this patent is extended or adjusted under 35 U.S.C. 154(b) by 0 days.

(21) Appl. No.: 12/897,376

(22) Filed: Oct. 4, 2010

(65) Prior Publication Data
US 2011/0085164 A1 Apr. 14, 2011

Related U.S. Application Data

(63) Continuation-in-part of application No. 12/273,169, filed on Nov. 18, 2008, now Pat. No. 7,808,634.

(51) Int. Cl.
*G01D 18/00* (2006.01)

(52) U.S. Cl.
USPC ........................................................ 250/252.1

(58) Field of Classification Search .......... 250/330–335, 250/336.1–336.2, 338.1–338.5, 339.01–339.15, 250/340, 341.1–341.8, 342–353, 252.1
See application file for complete search history.

(56) References Cited

U.S. PATENT DOCUMENTS

| | | | |
|---|---|---|---|
| 3,663,106 A | 5/1972 | Minami | |
| 3,767,925 A | 10/1973 | Foley | |
| 3,856,406 A | 12/1974 | Noble | |
| 5,455,673 A * | 10/1995 | Alsmeyer et al. | 356/301 |
| 5,822,058 A * | 10/1998 | Adler-Golden et al. | 356/303 |
| 5,850,623 A | 12/1998 | Carman | |
| 6,351,306 B1 | 2/2002 | Tedesco | |
| 6,353,656 B1 | 3/2002 | LeVert | |
| 6,573,990 B1 | 6/2003 | Anderson | |
| 7,808,634 B2 | 10/2010 | Nelson et al. | |
| 2002/0096636 A1 | 7/2002 | Ikeda | |
| 2002/0175287 A1 | 11/2002 | Busch | |
| 2003/0030797 A1 | 2/2003 | Palladino | |
| 2003/0038237 A1 | 2/2003 | Webber | |
| 2003/0052272 A1 | 3/2003 | Kiuchi | |
| 2003/0086159 A1 | 5/2003 | Suzuki | |
| 2003/0218745 A1 | 11/2003 | Benicewicz | |
| 2004/0127778 A1 | 7/2004 | Lambert | |
| 2004/0159789 A1 | 8/2004 | Treado | |
| 2004/0263843 A1 | 12/2004 | Knopp | |

(Continued)

OTHER PUBLICATIONS

Frost et al, "Calibration of Raman Spectrometer Instrument Response Function with Luminescence Standards: An Update," Applied Spectroscoy, 1988, col. 52, No. 12, p. 1614-1618.

(Continued)

*Primary Examiner* — Kiho Kim

(57) ABSTRACT

A method and apparatus for automated spectral calibration of a spectroscopy device. A method for simultaneous calibration and spectral imaging of a sample by: simultaneously illuminating the sample and a calibrant with a plurality of illuminating photons; receiving, at the spectrometer, a first plurality of photons collected from the sample and a second plurality of photons collected from the calibrant; forming a calibrant spectrum from the first plurality of collected photons and a sample spectrum from the second plurality of collected photons; comparing the calibrant spectrum with a reference spectrum of the calibrant to determine a wavelength-shift in the calibrant spectrum; applying the wavelength-shift to the sample spectrum to obtain a calibrated sample spectrum.

30 Claims, 6 Drawing Sheets

U.S. PATENT DOCUMENTS

| | | |
|---|---|---|
| 2005/0030657 A1 | 2/2005 | Maier |
| 2005/0162646 A1 | 7/2005 | Tedesco |
| 2005/0185179 A1 | 8/2005 | Wang |
| 2006/0001867 A1* | 1/2006 | Maier et al. .................. 356/301 |
| 2006/0001868 A1 | 1/2006 | Stewart |

OTHER PUBLICATIONS

International Searching Authority, International Search Report, US06/47933. Mar. 19. 2008, p. 1.

U S. Patent No. 7,808,634, Office Action, Feb. 5, 2010.

U.S. Patent No. 7,808,634 Office Action, Oct. 22, 2009.

U.S. Patent No. 7,808,634, Office Action, Jun. 15, 2009.

U.S. Patent Application Publication No. US20080034833, Office Action, Sep. 17, 2010.

U.S. Patent Application Pubfication No. US20080034833, Office Action,Mar. 23, 2010.

Webb et al, "Wavelength-Resolved 3-Dimensional Fluorescence Lifetime Imaging," 2002, Journal of Fluorescence, vol. 12, No. 2. pp. 273-283.

* cited by examiner

METHOD AND APPARATUS FOR AUTOMATED SPECTRAL CALIBRATION

RELATED APPLICATIONS

This application is a Continuation-in-Part to U.S. patent application Ser. No. 12/273, 169, entitled "Method and Apparatus for Automated Spectral Calibration," filed on Nov. 18, 2008, which itself claims priority to U.S. Provisional Patent Application No. 60/750,784 filed Dec. 16, 2005, and U.S. Provisional Patent Application No. 60/754,720 filed Dec. 29, 2005. The disclosure of each of these applications is incorporated herein in its entirety.

BACKGROUND

Conventional spectroscopic imaging systems are generally based on the application of high resolution, low aberration lenses and systems that produce images suitable for visual resolution by the human eye. These imaging systems include both microscopic spectral imaging systems as well as macroscopic imaging systems and use complex multi-element lenses designed for visual microscopy with high resolution aberrations optimized for each desired magnification. Spectroscopic imaging combines digital imaging and molecular spectroscopy techniques, which can include, Raman scattering, fluorescence, photoluminescence, ultraviolet, visible and infrared absorption spectroscopies. When applied to the chemical analysis of materials, spectroscopic imaging is commonly referred to as chemical imaging. Instruments for performing spectroscopic (i.e. chemical) imaging typically comprise image gathering optics, focal plane array (FPA) imaging detectors and imaging spectrometers.

The choice of FPA detector is governed by the spectroscopic technique employed to characterize the sample of interest. For example, silicon (Si) charge-coupled device (CCD) detectors, a type of FPA, are typically employed with visible wavelength fluorescence and Raman spectroscopic imaging systems, while indium gallium arsenide (InGaAs) FPA detectors are typically employed with near-infrared spectroscopic imaging systems. A variety of imaging spectrometers have been devised for spectroscopic imaging systems. Examples include, without limitation, grating spectrometers, filter wheels, Sagnac interferometers, Michelson interferometers and tunable filters such as acousto-optic tunable filters (AOTFs) and liquid crystal tunable filters (LCTFs).

The efficiency of the of imaging spectrometers is also a function of the system-specific noise caused by background light, room temperature, the wavelength of the scattered light and the electro-mechanical or optical intangibles associated with the spectrometer. For example, the LCTF has a wavelength dependent transmission modulation which affect's the accuracy and the efficiency of measuring sharp Raman bands with weak Raman scatterers. Experiments with certain LCTF devices show complicated interactions arising in the material and structure of the imaging devices produce a spatial and spectral modulation of light coming through the imaging device. The modulation produces an apparent background signal that is not uniform and masks the real signal.

Virtually all spectral imaging devices depend on the optical properties and transmission of light through one or more optical devices in order to produce the desired filtering effect. Such devices also have complex internal configuration which affects transmission of light through the device. Although the imaging filters are designed to minimize such aberrations, residual effects remain which limit the accuracy of the device and requiring the additional step of calibration prior to imaging the sample. However, implementing such sequential steps during examination of certain in vivo biological samples is inefficient, impractical and at times, impossible.

SUMMARY

In one embodiment, the disclosure relates to a method for simultaneous calibration and spectral imaging of a sample comprising: simultaneously illuminating the sample and a calibrant with a plurality of illuminating photons; receiving, at the spectrometer, a first plurality of photons collected from the sample and a second plurality of photons collected from the calibrant; forming a calibrant spectrum from the first plurality of collected photons and a sample spectrum from the second plurality of collected photons; comparing the calibrant spectrum With a reference spectrum of the calibrant to determine a wavelength-shift in the calibrant spectrum; applying the wavelength-shift to the sample spectrum to obtain a calibrated sample spectrum.

In another embodiment, the disclosure relates to a system for simultaneous calibration and dispersive and/or spectral imaging of a sample comprising: an input for simultaneously receiving a first plurality of photons collected from the sample and a second plurality of photons collected from a calibrant; a spectrograph for forming a sample spectrum from the first plurality of photons and a calibrant spectrum from the second plurality of photons; a first processor for comparing the calibrant spectrum with a reference spectrum of the calibrant to determine a wavelength-shift in the calibrant spectrum; and a second processor for applying the wavelength-shift to the sample spectrum to obtain a calibrated sample spectrum.

In still another embodiment, the disclosure relates to an apparatus for simultaneous calibration and dispersive and/or spectral image acquisition of a sample, comprising: a processing circuit for simultaneously receiving a calibrant spectrum and a sample spectrum, and a memory in communication with the processing circuit, the memory storing instructions for the processing circuit to: (i) process the calibrant spectrum to locate and identify a plurality of peaks, (ii) compare the plurality of peak locations in the calibrant spectrum with a plurality of corresponding peak locations in a reference spectrum of the calibrant, and (iii) determine a wavelength-shift as a function of a comparison between at least one peak location in the calibrant spectrum and a corresponding peak location in the reference spectrum; calibrate the sample spectrum by applying the wavelength-shift to the sample spectrum.

In another embodiment, the disclosure relates to a method for simultaneous calibration and imaging of a sample in a spectrometer, the method comprising: simultaneously illuminating the sample and an intrinsic calibrant with a plurality of illuminating photons; receiving, at the spectrometer, a first plurality of photons collected from the sample and a second plurality of photons collected from the intrinsic calibrant; forming a sample spectrum from the first plurality of photons and an intrinsic calibrant spectrum from the second plurality of photons; comparing the intrinsic calibrant spectrum with a reference spectrum for said intrinsic calibrant to determine a wavelength-shift in the calibrant spectrum; applying the wavelength-shift to the sample spectrum to obtain a calibrated sample.

In another embodiment, the disclosure relates to a system for simultaneous calibration and spectral imaging of a sample, the system comprising: an optical train containing an intrinsic calibrant and having a first optical path and a second optical path, the first optical path simultaneously illuminating the sample and the intrinsic calibrant with a plurality of illuminating photons and a second optical path collecting a first plurality of photons from the sample and a second plurality of photons from the intrinsic calibrant; a spectrograph for forming a sample spectrum from the first plurality of photons and an intrinsic calibrant spectrum from the second plurality of photons; a first processing circuitry for comparing the intrinsic calibrant spectrum with a reference spectrum for the intrinsic calibrant to determine a wavelength-shift; and a second processing circuitry for obtaining a calibrated sample spectrum by applying the wavelength-shift to the sample spectrum.

BRIEF DESCRIPTION OF THE DRAWINGS

Exemplary embodiments of the disclosure will be illustrated with reference to the following non-limiting illustrations in which.

DETAILED DESCRIPTION

The disclosure generally relates to a method and apparatus for automated spectral calibration of a spectroscopic device, The spectroscopic device can be used, for example, for Raman spectroscopy, visible absorption spectroscopy, near infrared absorption spectroscopy, infrared absorption spectroscopy, fluorescence spectroscopy or a combination thereof. The use of infrared spectroscopy may include at least one of: short wave infrared spectroscopy, mid wave infrared spectroscopy, and long wave infrared spectroscopy. Further, the spectroscopic device can include a conventional spectrometer configured according to the embodiments disclosed herein.

Figure 1:
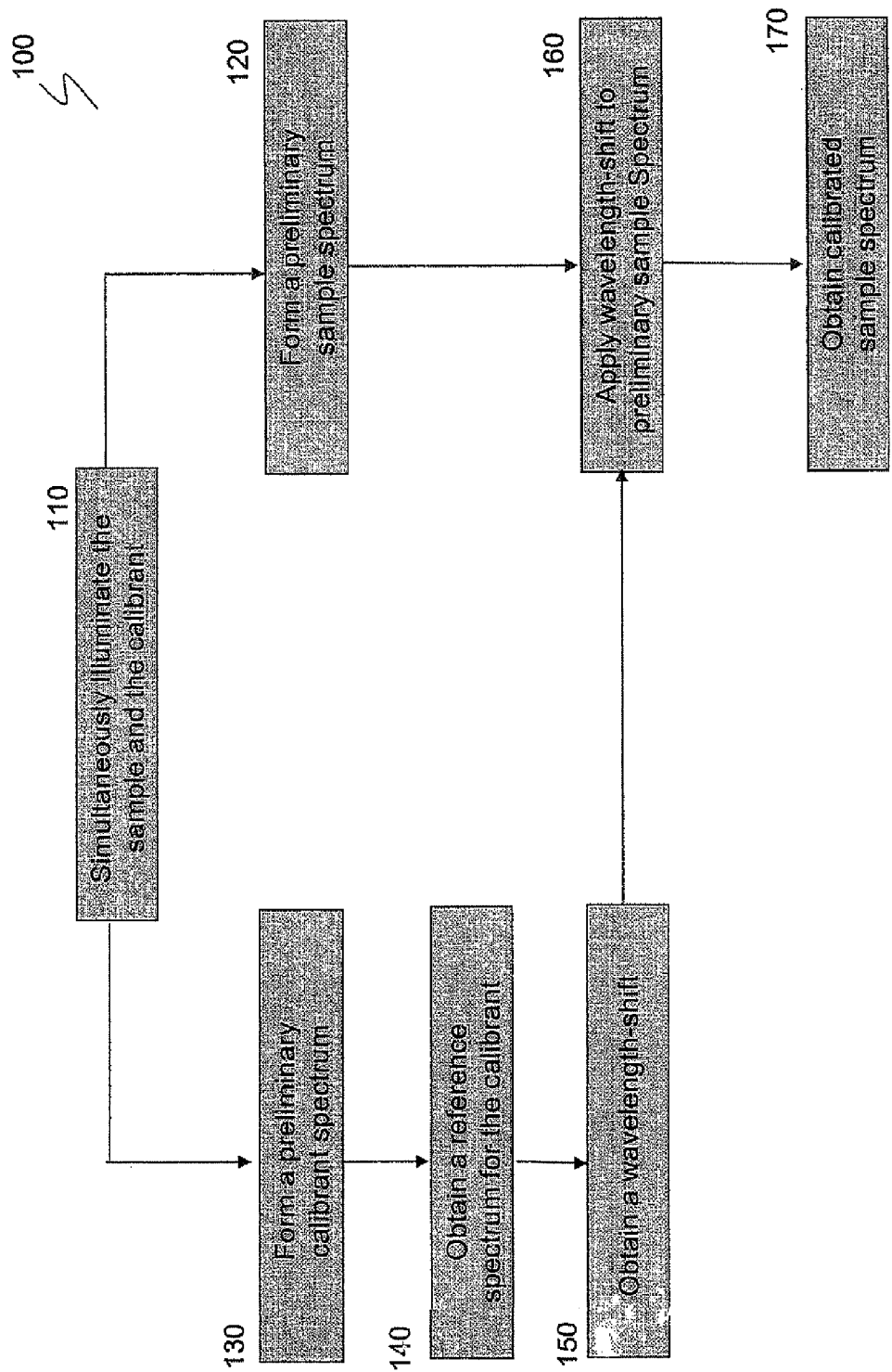
FIG. 1 is an exemplary algorithm according to one embodiment of the disclosure.

FIG. 1 is an exemplary algorithm according to one embodiment of the disclosure. In step 110 of algorithm 100, both the sample and the calibrant are illuminated simultaneously. The calibrant can be any reference material whose spectrum at a given wavelength or wave-number is known. The term "wavelength" or "wave-number" may apply to fluorescence, near-IR, IR or visible spectroscopy, but wavelength-shift or wave-number shift (interchangeably, Raman shift) conventionally applies to Raman spectroscopy. A non-exhaustive list of calibrants includes: acetaminophen, polymethyl methacrylate (PA), oxygen, nitrogen, neon, krypton, xenon, BK-7 glass, quartz, fused silica, naphthalene, 1,4 bis (2-methylstyryl) benzene, sulfur, toluene, acetonitrile, benzonitrile, cyclohexane, polystyrene, dysprosium oxide, and holmium oxide. Because the calibrant's spectrum at a given wavelength is known, it can be used as a baseline reference to calibrate the spectrometer.

The sample can be a chemical, a biological or any substance whose identity is detectable by spectroscopic analysis. Once illuminated, in steps 120 and 130 a preliminary spectrum of the sample and the calibrant can be obtained. Steps 120 and 130 can be implemented simultaneously or sequentially. In step 140, a reference spectrum for the calibrant is obtained having well-known peak position (i.e., wavelength) values.

As will be discussed below, each of the reference and measured spectra of the calibrant can include a plurality of intensity peaks. A comparison of the location of the peaks in the reference spectrum with the corresponding peaks in the calibrant's measured spectrum can reveal a wavelength-shift as shown in step 150.

In step 160 the wavelength-shift is applied to the preliminary sample spectrum. By adjusting the preliminary sample spectrum 120 commensurate with the wavelength-shift 150, a calibrated sample spectrum 170 can be obtained. As stated, steps 120 and 130 can be implemented simultaneously or sequentially. In an embodiment of the disclosure, steps 130-150 are implemented followed by steps 120, 160 and 170.

Figure 2:
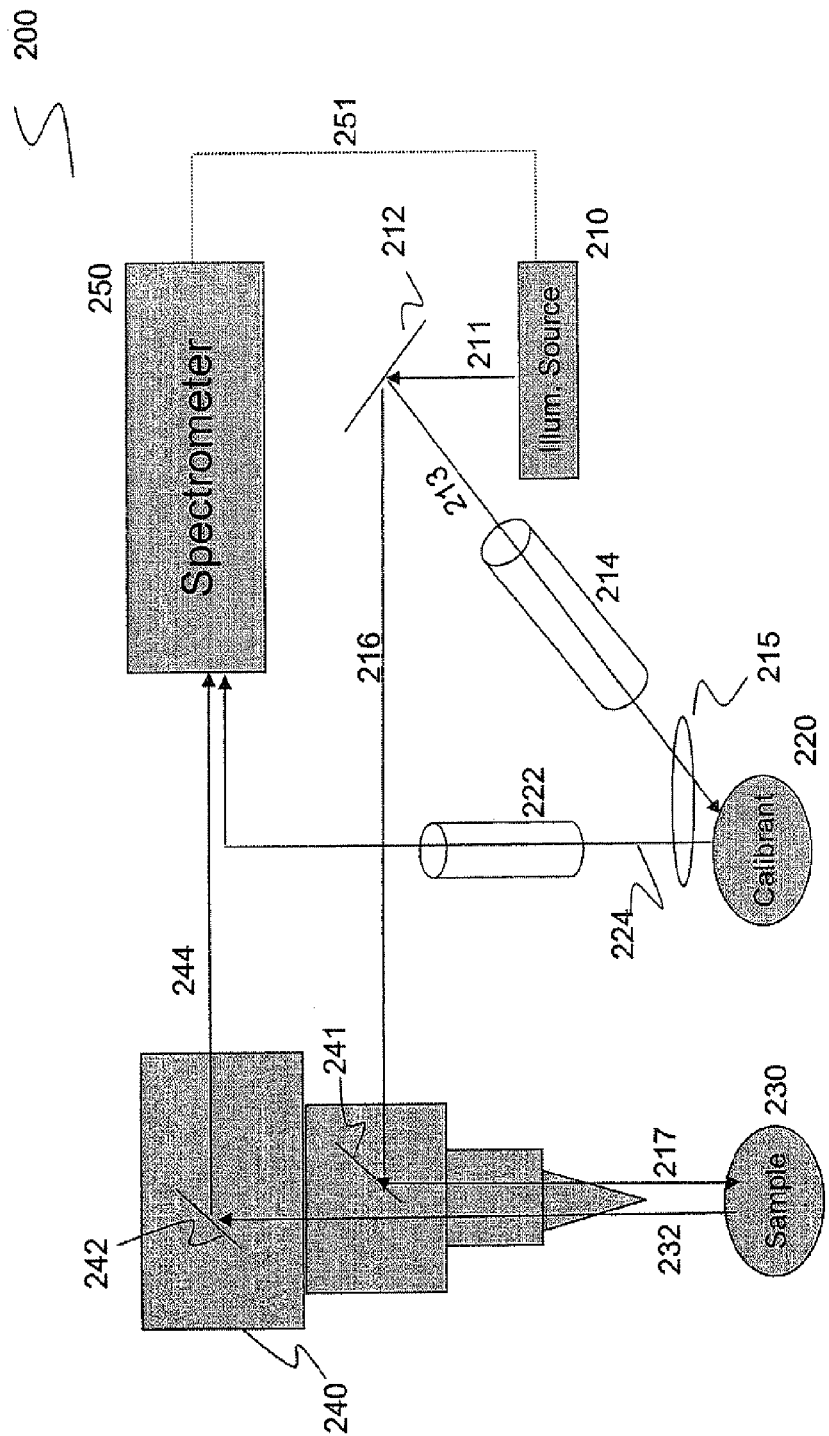
FIG. 2 is an exemplary auto-calibration system according to one embodiment of the disclosure.

FIG. 2 is an exemplary auto-calibration system according to one embodiment of the disclosure. System 200 of FIG. 2 includes, among others, illumination source 210, calibrant 220, sample 230, optical train 240 and spectrometer 250. Illumination source 210 can be any source appropriate for making a Raman, fluorescence, visible absorption/reflectance, infrared (IR) absorption/reflectance and/or near IR absorption/reflectance measurement.

Illumination source 210 directs photons 211 to optical splitter 212 which can direct a first group of the illuminating photons 216 to sample 230 by way of mirror or beam splitting element 241. Optical splitter 212 can also direct a second group of illuminating photons 213 to calibrant 220. In one embodiment illuminating photons 212 are directed through an optical medium, such as optical fiber 214. In another embodiment, illuminating photons can be filtered through optical lens 215 prior to illuminating calibrant 224. In still another embodiment (not shown), optical lens 215 is positioned to only filter photons 224 collected from calibrant 220.

Depending on the illumination properties, photons 224 interacting with calibrant 220 can be reflected, refracted, emitted, scattered, transmitted and/or absorbed by the calibrant. Collected photons 224 can optionally be directed to spectrometer 250 through optical fiber 222. In one embodiment, one or more optical fibers can carry light from the calibrant to the spectrometer and one or more optical fibers can carry light from the sample to the spectrometer. The fibers can be inserted in parallel into the entrance slit of the spectrograph. Spectrometer 250 can form a preliminary calibrant spectrum for comparison with a reference calibrant spectrum.

Similarly, illuminating photons 216 can be directed to mirror 241 for illuminating sample 230 with photons 217. Sample illumination can be direct (not shown) or it can take place through optical train 240. Collected photons 232 from sample 230 can be directed to spectrometer 250 through gathering optical train 240 and mirror 242. Optical train 240 can have one or more optical filters (not shown) for removing photons of undesired wavelength from group of photons collected from sample 232. In addition, photons collected from the sample 232 can be photons that are reflected, refracted, emitted, scattered, transmitted, and absorbed.

As stated, photons 244 and 224 can be directed to spectrometer 250 through fiber optic medium (not shown). Such medium can comprise a plurality of optical fibers assembled for communication with spectrometer 250. In one embodiment, the optical fiber can define a bifurcated fiber optic line having a first optical medium and a second optical medium positioned adjacent to one another. Thus, a first optical medium communicates photons 244 collected from the sample to spectrometer 250 while the second optical medium independently communicates photons 224 collected from the calibrant.

Once photons 224 are received at spectrometer 250, a preliminary calibrant spectrum can be formed. The preliminary calibrant spectrum can be compared with a reference calibrant spectrum to determine a wavelength-shift as discussed in relation to FIG. 1. In one embodiment, spectrometer 250 and illumination source 210 communicate the illumination wavelength 251 to each other.

Spectrometer 250, having received photons 244 collected from sample 230 can form a preliminary sample spectrum. Applying the wavelength-shift to the preliminary sample spectrum, can result in a calibrated spectrum/image for sample 230. The operation of an exemplary spectrometer will be discussed further below.

Figure 3:
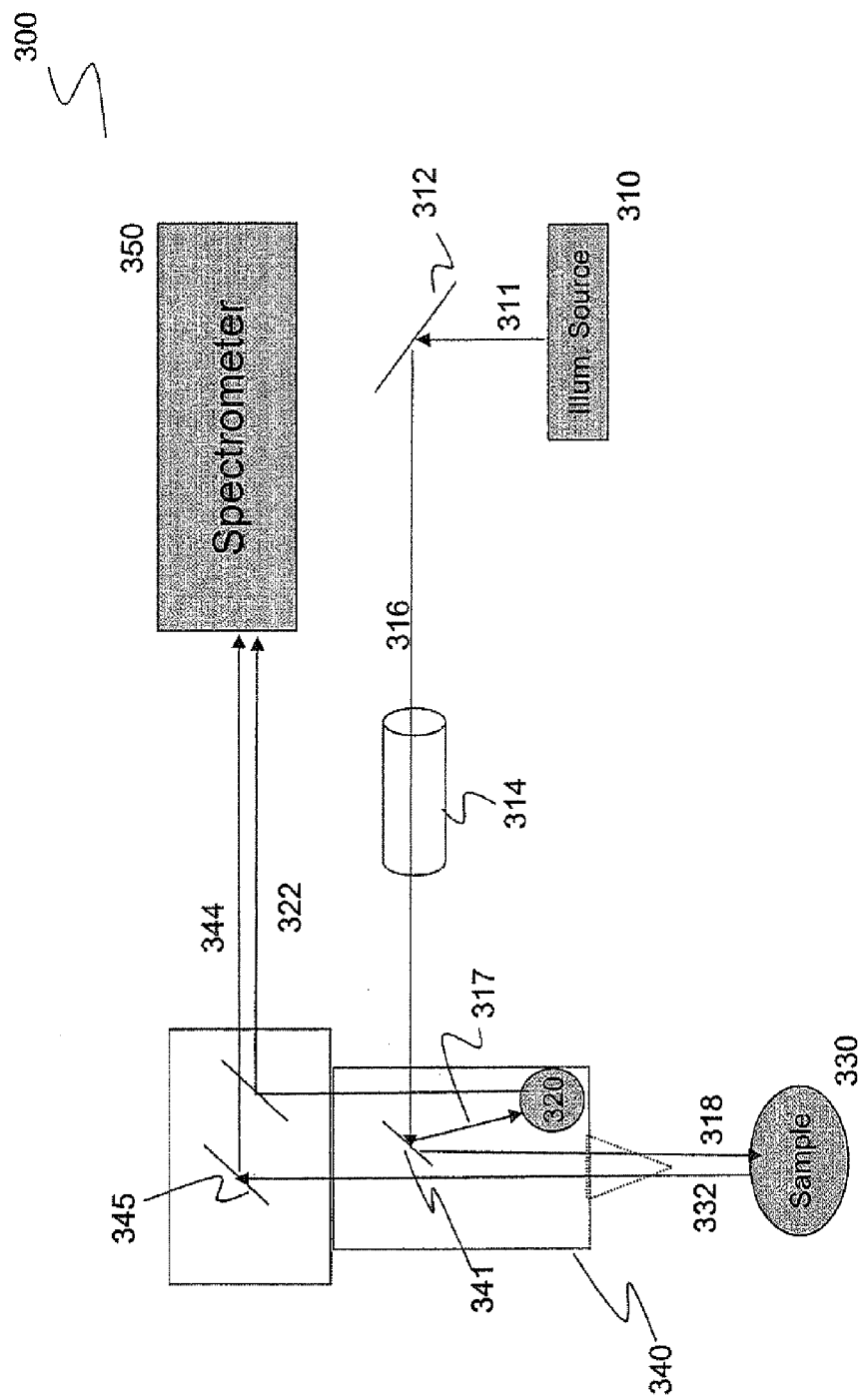
FIG. 3 is an exemplary auto-calibration system according to another embodiment of the disclosure.

FIG. 3 is an exemplary auto-calibration system according to another embodiment of the disclosure. In FIG. 3, system 300 includes, among others, illumination source 310, calibrant 320, sample 330, optical train 340 and spectrometer 350. Optical train 340 is configured to receive calibrant 320 to largely eliminate the need for a separate calibrant illumination circuit. Referring to FIG. 3, illuminating photons 311 are directed 316 through mirror or beam splitting element 312 and through optical medium 314. Splitting optics 341 directs a first plurality of illuminating photons 318 to sample 330 while directing a second plurality of illuminating photons 317 to calibrant 320.

In one embodiment, optical train 340 is configured with a compartment for receiving calibrant 320. Such compartment can be devised to provide easy access to calibrant 320. For example, if a solid calibrant such as acetaminophen is used, optical train 340 can be configured to have a compartment for receiving calibrant 320. Depending on the nature of the calibrant, it may also be composed of or coated on an optical lens of optical train 340. For example, if the calibrant is a polymer material such as PMMA, it can be composed of or coated on a lens of optical train 340. Such materials can be used to automatically calibrate the spectrometer without sacrificing the ability to make a spectroscopic measurement.

Figure 4:
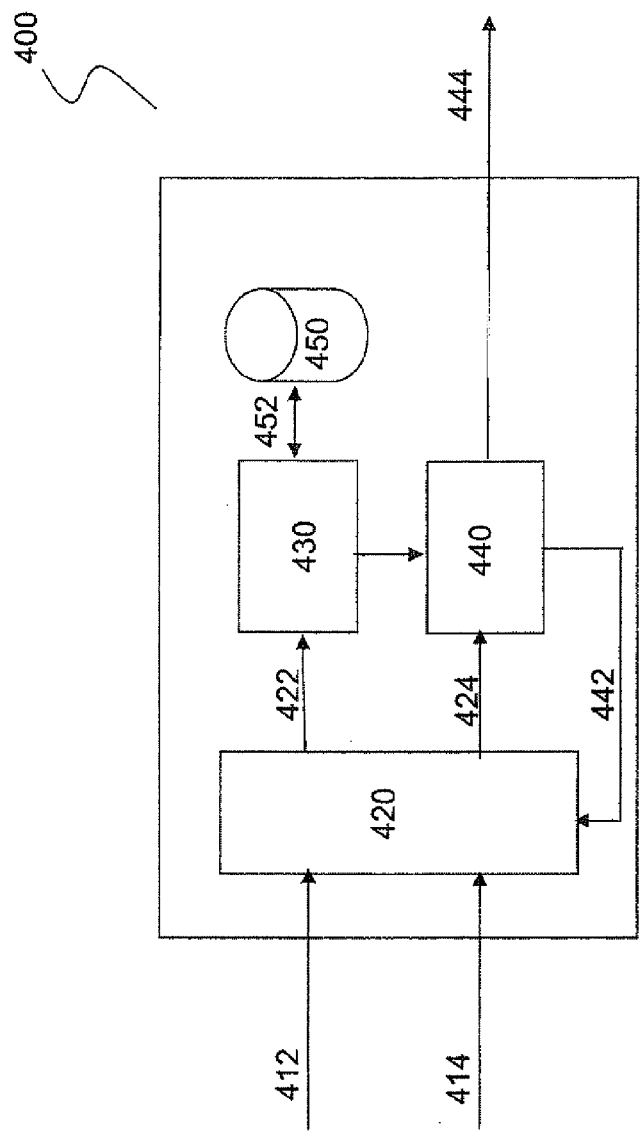
FIG. 4 is a representative spectrometer in accordance with an embodiment of the disclosure.

Photons 322 collected from the calibrant 320 can be directed to spectrometer 350 along with photons 332, 344 collected from the sample 332. One or more optical mediums (not shown) and mirrors or beam-splitters 345 can be configured to communicate the collected photons to spectrometer 350. Additional filters and lenses can be used to further remove photons of unwanted wavelength before delivering the collected photons to spectrometer 350. Spectrometer 350 can form a preliminary sample spectrum and a preliminary calibrant spectrum (not shown). A wavelength-shift can be determined by comparing the preliminary calibrant spectrum with a reference spectrum for the calibrant. Once determined, the wavelength-shift can be applied to the sample spectrum to determine a calibrated sample spectrum for sample 330. FIG. 4 is a representative spectrometer in accordance with an embodiment of the disclosure. In FIG. 4, system 400 receives photons collected from the sample 414 and photons collected from the calibrant 412 at spectrograph 420. Spectrograph 420 forms a preliminary calibrant spectrum 422 and a preliminary sample spectrum 424. The preliminary sample spectrum 422 can be directed to first processor 430. Processor 430 also receives a reference spectrum 452 from database 450. By comparing reference spectrum 452 with preliminary calibrant spectrum 422, processor 430 can determine a wavelength-shift.

First processor 430 communicates wavelength-shift to second processor 440. Second processor 440, having received sample spectrum 440 from spectrograph 420, can apply the wavelength shift 442 to sample spectrum to obtain a calibrated sample spectrum. The calibrated sample spectrum can be reported 444 from spectrometer 400.

It should be noted that FIG. 4 provides an exemplary functional representation and is not intended to limit the scope of the disclosure. For example, the detector associated with spectrograph 420 can communicate the sample- or calibrant-collected photons (414, 412, respectively) to a central processing unit via an analog-to-digital converter. The detector may be a photodiode array, a charge-coupled device (CCD) or a focal plane array. Spectrograph 420 may alternatively be a liquid crystal tunable filter (LCTF) or similar device coupled with one or more of the for mentioned detector types for spectroscopic imaging. Such devices can operate in connection with a software program applying the wavelength-shift to the preliminary spectra to obtain calibrated spectra.

In one embodiment, the spectrograph 420 may comprise a multi-conjugate liquid crystal tunable filter. In one embodiment, this multi-conjugate liquid crystal tunable filter may comprise multi-conjugate filter technology available from ChemImage Corporation, Pittsburgh, Pa. This technology is more fully described in the following U.S. patents and U.S. patent application Nos, which are hereby incorporated by reference in their entireties: U.S. Pat. No. 7,362,489, filed on Apr. 22, 2005, entitled "Multi-conjugate liquid crystal tunable filter" and U.S. Pat. No. 6,992,809, filed on Feb. 2, 2005, also entitled "Multi-conjugate liquid crystal tunable filter."

Further, first processor 430 and second processor 440 can be combined into one processor (not shown) under the control of a software application (not shown). Alternatively, the first and second processors can define one or more firmware devices. Database 450 can be a look-up table stored in a memory (not shown). The processors and the memory can control optical device such as a photodiode array, a CCD or an LCTF. Further, the optical device can provide a spatially accurate wavelength-resolved image of the sample showing a first and a second spatial dimension. A spatially accurate wavelength-resolved image is an image of a sample that is formed from multiple "frames" wherein each frame has plural spatial dimensions and is created from photons of a particular wavelength (or wave number) or from photons in a particular wavelength band (or wave number band) so that the frames may be combined to form a complete image across all wavelengths (wave numbers) of interest.

As discussed, suitable polymeric calibrants (e.g., PMMA) can be coated directly on a lens (or a portion of the lens) of the gathering optics to provide means for automatic calibration. The gathering lens can be part of the optical train associated with the spectrometer. Coating the calibrant on the gathering lens does not necessarily inhibit one's ability to acquire a spectrum of the sample.

Figure 5:
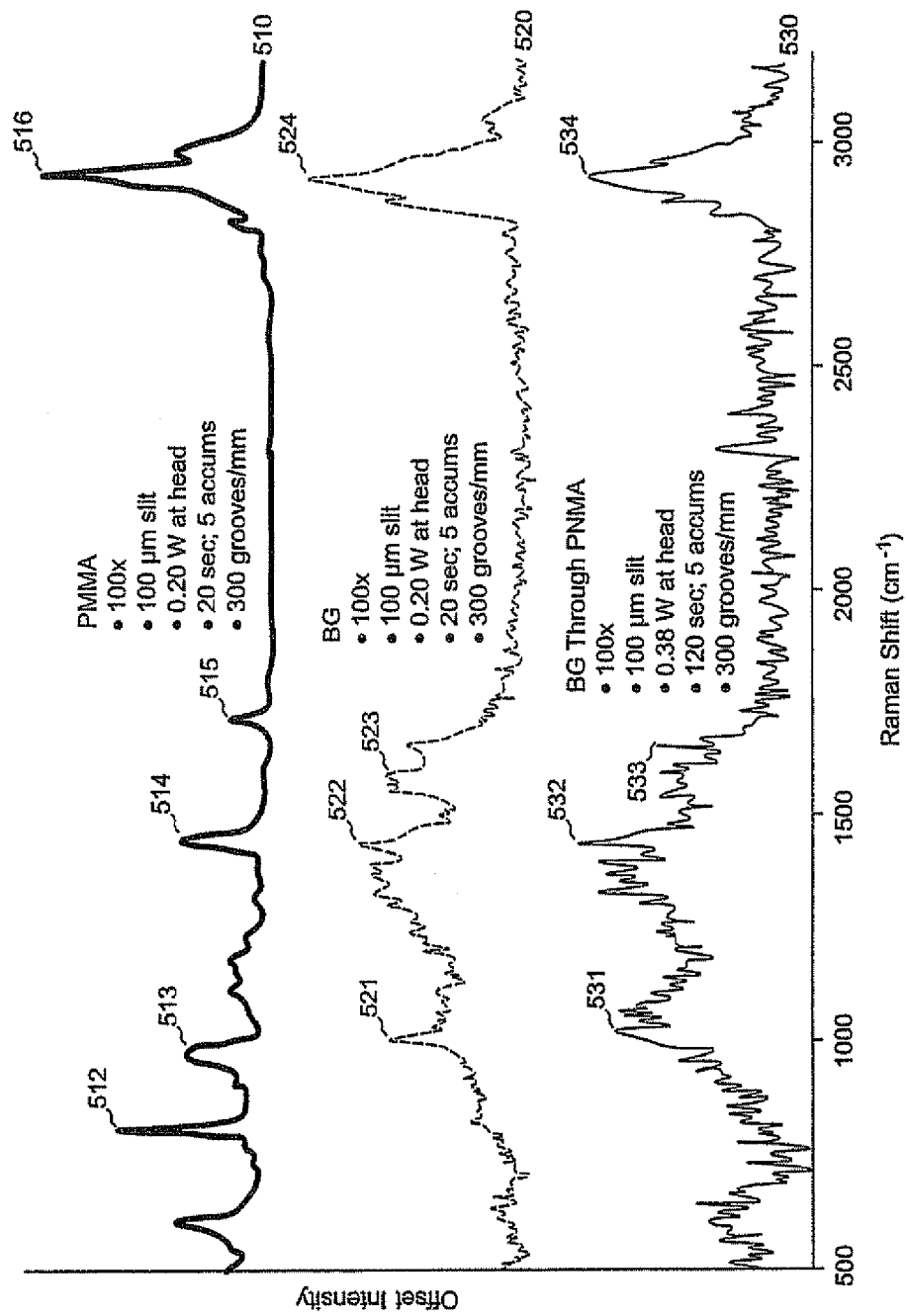
FIG. 5 shows dispersive Raman spectra of a calibrant and a sample according to one embodiment of the disclosure.

FIG. 5 shows a dispersive Raman spectroscopy of a calibrant and a sample according to one embodiment of the disclosure. Referring to FIG. 5, spectrum 510 is the Raman spectrum for calibrant PMMA. Spectrum 510 shows Raman intensity peaks 512, 513, 514, 515 and 516, each of which has been wavelength-shifted to account for the system calibration. Spectrum 520 represent sample spectrum for Bacillus Globigii (BG) spores. Bacillus globigii spores have been used as an anthrax simulant. Spectrum 520 shows Raman intensity peaks 521, 522, 523 and 524. Each of spectra 510 and 520 were collected using gathering optics which was not coated with PMMA.

Spectrum 530 shows BG spectrum collected while having PMMA in the excitation/collection optical path. Spectrum 530 shows Raman intensity peaks 531, 532, 533 and 534. As seen in FIG. 5, peaks 531, 532, 533 and 534 are substantially at the same Raman wavelength shift as the corresponding Raman intensity peaks of spectrum 520. It is evident from FIG. 5 that coating one or more gathering lens of an optical train does not impair the ability to collect a recognizable sample's spectrum.

Figure 6:
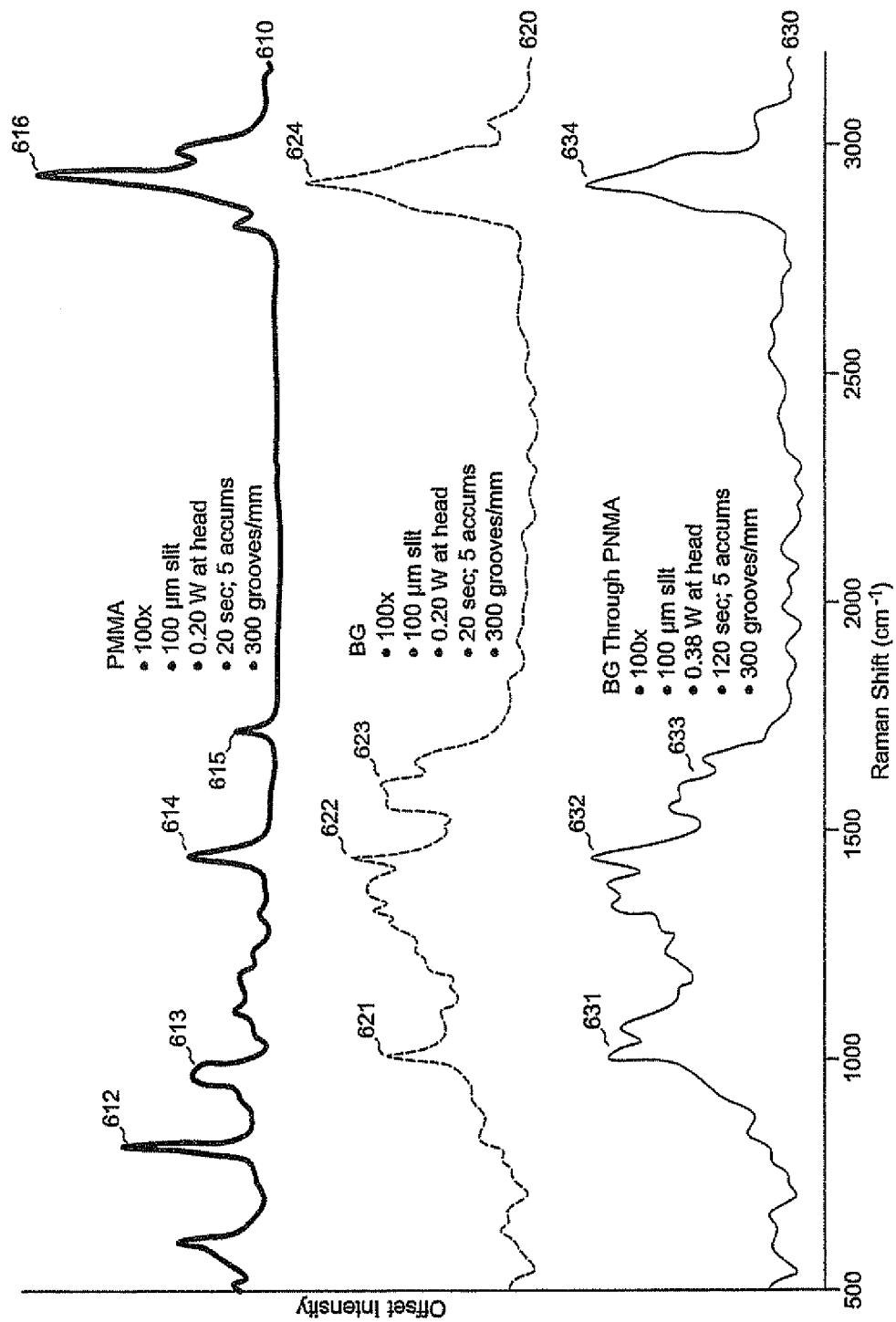
FIG. 6 shows filtered (smoothed) dispersive Raman spectra for the calibrant and the sample of FIG. 5.

FIG. 6 shows a filtered (smoothed) dispersive Raman spectra for the calibrant and the sample of FIG. 5. FIG. 5 has been filtered to improve the signal-to-noise ratio of the data. Raman intensity peaks 612, 613, 614, 615 and 616 of spectrum 610 are consistent with the respective. Raman intensity peaks of spectrometer 510. Similarly, Raman intensity peaks 621, 622, 623 and 624 are consistent with Raman intensity peaks 521, 522, 523 and 524, respectively, of spectrum 520. Finally, Raman spectrum 630 is consistent with unfiltered Raman spectrum 530 as each of Raman intensity peaks 631, 632, 633 and 634 corresponds with Raman intensity peaks 531, 532, 533 and 534. The filtered spectra of FIG. 6 further show that coating an optical lens with a calibrant will not impair the ability to collect a recognizable sample's spectrum. The above description is not intended and should not be construed to be limited to the examples given but should be granted the full breadth of protection afforded by the appended claims and equivalents thereto. Although the disclosure is described using illustrative embodiments provided herein, it should be understood that the principles of the disclosure are not limited thereto and may include modification thereto and permutations thereof.

What is claimed is:

1. A method for simultaneous calibration and spectral imaging of a sample comprising:
   simultaneously illuminating the sample and an intrinsic calibrant with a plurality of illuminating photons from a single source;
   receiving, at a spectrometer, a first plurality of photons collected from the sample and a second plurality of photons collected from the calibrant;
   forming a calibrant spectrum from the second plurality of collected photons and a sample spectrum from the first plurality of collected photons, wherein said sample spectrum comprises a Raman spectrum;
   directing the calibrant spectrum to a first processor and the sample spectrum to a second processor;
   configuring the first processor to compare the calibrant spectrum with a reference spectrum of the calibrant to determine a wavelength-shift in the calibrant spectrum;
   configuring the second processor to apply the wavelength-shift to the sample spectrum to obtain a calibrated sample spectrum; and
   forming a spatially-accurate wavelength resolved Raman image of the sample.

2. The method of claim 1, wherein the photons collected from the sample are selected from the group consisting of photons reflected, refracted, emitted, scattered, transmitted and absorbed by the sample.

3. The method of claim 1, wherein the calibrant is selected from the group consisting of acetaminophen, polymethyl methacrylate, oxygen and nitrogen, neon, krypton, xenon, BK-7 glass, quartz, fused silica, naphthalene, 1,4 bis (2-methylstyryl) benzene, sulfur, toluene, acetonitrile, benzonitrile, cyclohexane, polystyrene, dysprosium oxide, and holmium oxide.

4. The method of claim 1, wherein the spectrometer is a dispersive spectrometer.

5. The method of claim 1, wherein the spectrometer is an imaging spectrometer.

6. The method of claim 5, wherein the imaging spectrometer includes at least one of: a liquid crystal tunable filter and a multi-conjugate liquid crystal tunable filter.

7. The method of claim 1, wherein the plurality of illuminating photons have a first Wavelength.

8. The method of claim 1, wherein the step of receiving the plurality of photons collected from the sample and the plurality of photons collected from the calibrant further comprises separating the photons collected from the sample from the photons collected from the calibrant.

9. The method of claim 1, wherein the step of receiving the plurality of photons collected from the sample and the plurality of photons collected from the calibrant further comprises filtering the received photons to remove photons of an undesired wavelength.

10. A system for simultaneous calibration and dispersive and/or spectral imaging of a sample comprising:
    an input for simultaneously receiving a first plurality of photons collected from the sample and a second plurality of photons collected from an intrinsic calibrant, wherein said first plurality of photons and said second plurality of photons originate from the same source;
    a Raman spectrometer for forming a sample spectrum from the first plurality of photons and a calibrant spectrum from the second plurality of photons;
    a first processor for comparing the calibrant spectrum with a reference spectrum of the calibrant to determine a wavelength-shift in the calibrant spectrum;
    a second processor for applying the wavelength-shift to the sample spectrum to obtain a calibrated sample spectrum; and
    a detector for generating a spatially-accurate wavelength resolved Raman image of the sample.

11. The system of claim 10, wherein the photons collected from the sample are selected from the group consisting of photons reflected, refracted, luminesced, fluoresced, Raman scattered, transmitted, absorbed, and emitted by the sample.

12. The system of claim 10, wherein the first processor is programmed with instructions to: a) determine a plurality of peak locations in the calibrant spectrum; b) determine a plurality of peak locations in the reference spectrum of the calibrant; c) compare the plurality of peak locations in the calibrant spectrum with a plurality of corresponding peak locations in the reference spectrum of the calibrant; and d) determine the wavelength-shift as a function of the comparison between at least one peak location in the calibrant spectrum and a corresponding peak location in the reference spectrum.

13. e system of claim 10, wherein the spectrometer is a dispersive spectrometer.

14. The system of claim 10, further comprising a first medium for communicating the first plurality of photons collected from the sample and a second medium for communicating the second plurality of photons collected from the calibrant.

15. An apparatus for simultaneous calibration and dispersive and/or spectral image acquisition of a sample, comprising:
    a first processing circuit for simultaneously receiving a calibrant spectrum and a sample spectrum wherein,
    said calibrant comprises an intrinsic calibrant,
    said calibrant spectrum and said sample spectrum are formed using photons from a single source, and
    said sample spectrum comprises a Raman spectrum; and
    a memory in communication with the processing circuit, the memory storing instructions for the processing circuit to: process the calibrant spectrum to locate and identify a plurality of peaks, compare the plurality of peak locations in the calibrant spectrum with a plurality of corresponding peak locations in a reference spectrum of the calibrant, and determine a wavelength-shift as a function of a comparison between at least one peak location in the calibrant spectrum and a corresponding peak location in the reference spectrum;

a second processing circuit configured to calibrate the sample spectrum by applying the wavelength-shift to the sample spectrum; and forming a spatially-accurate wavelength resolved Raman image.

16. The apparatus of claim 15, wherein applying the wavelength-shift further comprises: (a) identifying a plurality of peak locations in the sample spectrum; and (b) applying the wavelength-shift to at least one of the plurality of peak locations in the sample spectrum.

17. The apparatus of claim 15, further comprising a database for storing a reference spectrum of the calibrant.

18. The apparatus of claim 15, wherein the processing circuit comprises at least one microprocessor.

19. The apparatus of claim 15, wherein the apparatus is a spectrometer.

20. The apparatus of claim 19, wherein the spectrometer is a dispersive spectrometer.

21. The apparatus of claim 19, wherein the spectrometer is an imaging spectrometer.

22. The apparatus of claim 21, wherein the imaging spectrometer includes at least one of: a liquid crystal tunable filter and a multi-conjugate liquid crystal tunable filter.

23. The apparatus of claim 15, wherein the calibrant is selected from the group consisting of acetaminophen, polymethyl methacrylate, oxygen and nitrogen, neon, krypton, xenon, BK-7 glass, quartz, fused silica, naphthalene, 1,4 bis (2-methylstyryl) benzene, sulfur, toluene, acetonitrile, benzonitrile, cyclohexane, polystyrene, dysprosium oxide, and holmium oxide.

24. A method for simultaneous calibration and imaging of a sample in a spectrometer, the method comprising:

simultaneously illuminating the sample and an intrinsic calibrant with a plurality of illuminating photons from a single source;

receiving, at a spectrometer, a first plurality of photons collected from the sample and a second plurality of photons collected from the intrinsic calibrant;

forming a sample spectrum from the first plurality of photons, wherein said sample spectrum comprises a Raman spectrum, and an intrinsic calibrant spectrum from the second plurality of photons;

configuring a first processor to compare the intrinsic calibrant spectrum with a reference spectrum for said intrinsic calibrant to determine a wavelength-shift in the calibrant spectrum;

configuring a second processor to apply the wavelength-shift to the sample spectrum to obtain a calibrated sample spectrum; and forming a spatially-accurate wavelength resolved Raman image of the sample.

25. The method of claim 24, wherein imaging defines at least one of obtaining dispersive spectral data or spectral imaging data from the sample.

26. The method of claim 24, wherein the first plurality of photons collected from the sample are selected from the group consisting of photons reflected, refracted, luminescence-emitted, fluorescence-emitted, Raman scattered, transmitted, absorbed, and emitted by the sample.

27. The method of claim 24, wherein the intrinsic calibrant selected from the group consisting of acetaminophen, polymethyl methacrylate, oxygen and nitrogen, neon, krypton, xenon, BK-7 glass, quartz, fused silica, naphthalene, 1,4 bis (2-methylstyryl) benzene, sulfur, toluene, acetonitrile, benzonitrile, cyclohexane, polystyrene, dysprosium oxide, and holmium oxide.

28. The method of claim 24, wherein the spectrometer is a dispersive spectrometer.

29. The method of claim 24, wherein the spectrometer is an imaging spectrometer.

30. The method of claim 29, wherein the imaging spectrometer includes at least one of a liquid crystal tunable filter and a multi-conjugate liquid crystal tunable filter.

* * * * *